United States Patent [19]

Radisson

[11] Patent Number: 4,873,343

[45] Date of Patent: Oct. 10, 1989

[54] PROCESS FOR THE PREPARATION OF N-(2-CHLOROBENZYL)-2-(2-THIENYL) ETHYLAMINE

[75] Inventor: Joël Radisson, Toulouse, France

[73] Assignee: Sanofi, Paris, France

[21] Appl. No.: 275,369

[22] Filed: Nov. 23, 1988

[30] Foreign Application Priority Data

Dec. 18, 1987 [FR] France ................................ 87 17755

[51] Int. Cl.$^4$ .......................................... C07D 333/12
[52] U.S. Cl. ..................................... 549/74
[58] Field of Search .......................................... 549/74

[56] References Cited

U.S. PATENT DOCUMENTS 4,458,086  7/1984  Chekroun et al. .................... 549/74

FOREIGN PATENT DOCUMENTS 2300090  9/1976  France .

OTHER PUBLICATIONS

Campaigne, E. and Walter C. McCarthy, "3-Substituted Thiophenes, VIII, 3-Thienylalkylamines", Journal of the American Chemical Society, vol. 76, No. 17, Sep. 9, 1954, pp. 4466-4468.

Primary Examiner—Alan Siegel
Attorney, Agent, or Firm—Wegner & Bretschneider

[57] ABSTRACT

In the process according to the invention 2-thiophene acetonitrile is reacted with 2-chlorobenzylamine and hydrogen in the presence of a hydrogenation catalyst.

The product obtained is a chemical intermediate useful in the pharmaceutical industry.

9 Claims, No Drawings

PROCESS FOR THE PREPARATION OF N-(2-CHLOROBENZYL)-2-(2-THIENYL) ETHYLAMINE

The present invention relates to a process for the preparation of N-(2-chlorobenzyl)-2-(2-thienyl)ethylamine starting from 2-thiophene acetonitrile.

This secondary amine was described for the first time in French Pat. No. 2 300 090 as an intermediate in the synthesis of a compound of formula:

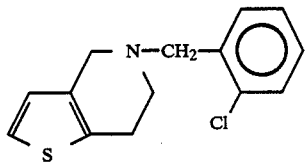

a platelet aggregation inhibitor, the international nonpropriety name of which is ticlopidine.

The process for the preparation of N-(2-chlorobenzyl)-2-(2-thienyl)-ethylamine of the formula:

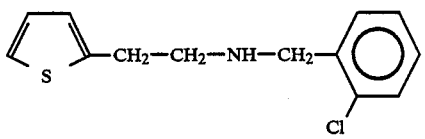

described in French Pat. No. 2 300 090 consists in reacting 2-chlorobenzylamine with 2-(2-thienyl)ethyl benzenesulfonate according to the reaction scheme:

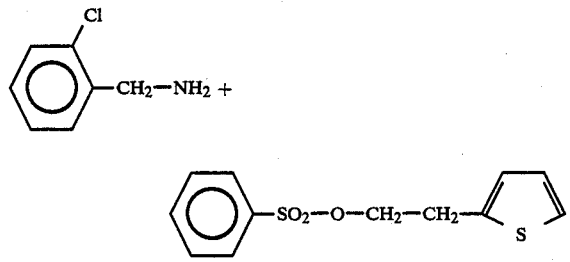

The above amine is available on an industrial scale but the sulfonate has to be prepared from 2-(2-thienyl)ethanol, obtained by the action of ethylene oxide on the organolithium compound:

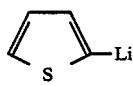

Although the yields of the successive steps are satisfactory, the overall process is expensive, especially as the first step implies working under rigorously anhydrous conditions.

It has now been found, and this is the object of the invention, that the compound of formula I can be prepared in good yields by reaction of 2-thiophene acetonitrile with 2-chlorobenzylamine and hydrogen in the presence of a hydrogenation catalyst, according to the reaction scheme:

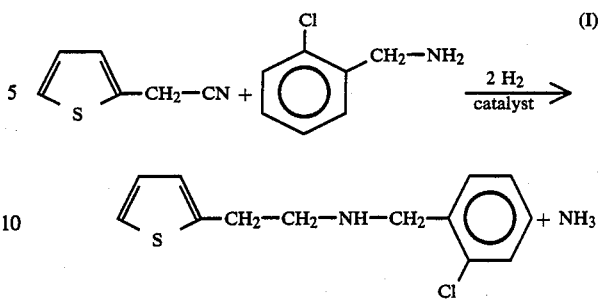

Since 2-thiophene acetonilitrile and 2-chlorobenzylamine are commercially available compounds, the access to the compound of formula (I) is made more direct.

The catalyst used is a common hydrogenation catalyst. It is preferably Raney nickel or palladium deposited on a porous inert support, such as active charcoal.

The pressure during the hydrogenation usually is between 10 and 100 bars (between 1 and 10 MPa), and preferably between 25 and 70 bars (between 2.5 and 7 MPa).

The temperature of the reaction is usually lower than 80° C., and preferably between 40° and 60° C.

The reaction may be carried out without a solvent or in an inert organic solvent which dissolves the reagents and hydrogen, such as alcohols, and preferably methanol. The molar ratio of the reagents:

2-chlorobenzylamine
2-thiophene acetonitrile may be selected between 1 and 5, and preferably between 1 and 2 in the case of palladium as catalyst, and preferably between 2 and 4 in the case of Raney nickel.

The reagents may be mixed before the introduction of hydrogen, or the 2-thiophene acetonitrile may be added gradually to the 2-chlorobenzylamine in the presence of the catalyst and hydrogen.

The N-(2-chlorobenzyl)-2(2-thienyl)ethylamine may be isolated from the reaction mixture by distillation under reduced pressure or by the precipitation of one of its salts, such as the hydrochloride.

The excess of 2-chlorobenzylamine may be recovered either by distillation under reduced pressure from the reaction mixture, or through salt formation, the salt of (I) being recovered from their mixture due to their different solubilities in aqueous media. In particular in the medium constituted by isopropyl ether and water, the hydrochloride of (I) precipitates whereas the hydrochloride of 2-chlorobenzylamine remains in the aqueous phase.

The following examples illustrate the invention.

EXAMPLE 1

100 g (0.81 mole) of 2-thiophene acetonitrile, 350 g (2.473 moles) of 2-chlorobenzylamine and 25 g of Raney nickel are introduced into a hydrogenation reaction vessel of 3500 ml capacity.

The volume is adjusted to 1500 ml by means of methanol and the reaction mixture is hydrogenated at 50° C. at a pressure of 35 bars + 5 bars (3.5 ± 0.5 MPa).

When the theoretical amount of hydrogen has been taken up, the catalyst is filtered off, the solvent is evaporated and the residue is distilled under a pressure of 0.3 mm Hg (40 Pa).

The remaining 2-chlorobenzylamine distills between 60° and 65° C. at this pressure, followed by the N-(2- chlorobenzyl)-2-(2-thienyl)ethylamine between 120° and 130° C. In this way 150 g of the expected product are obtained, corresponding to a yield of 74.5% with respect to the 2-thiophene acetonitrile introduced.

The elemental analysis and the infra-red spectrum of the product isolated are as expected.

EXAMPLE 2

20 g (0.16 mole) of 2-thiophene acetonitrile, 56.8 g (0.40 mole) of 2-chlorobenzylamine, 8 g of Raney nickel and 120 ml of methanol are introduced into a hydrogenation reaction vessel of 500 ml capacity. The reaction mixture is hydrogenated at 50° C. at a pressure of 35 bars+5 bars (3.5±0.5 MPa).

When the theoretical amount of hydrogen has been taken up, the catalyst is filtered off and the solvent is evaporated in a vacuum.

The residue is taken up in 200 ml of isopropyl ether and the mixture is stirred for 1 h at 0° C. with 100 ml of 6N hydrochloric acid. The product which crystallized is filtered off, washed with water, then with isopropyl ether and acetone and is dried to constant weight at 50° C. 35.5 g of the hydrochloride of N-(2-chlorobenzyl)-2-(2-thienyl)ethylamine are obtained. M.p.=145°-147° C.

Yield: 72% with respect to the 2-thiophene acetonitrile introduced.

Infra-red spectra:

| | |
|---|---|
| 3330 cm$^{-1}$: | $\nu$NH |
| 3150 cm$^{-1}$: | $\nu$CH (thiophene) |
| 3060 cm$^{-1}$: | $\nu$CH (benzene) |
| 2940 cm$^{-1}$: | $\nu$CH$_2$ |
| 2850–2200 cm$^{-1}$: |  |
| 1590 et 1480 cm$^{-1}$: | C—C (benzene) |
| 1450 cm$^{-1}$: | C—C (thiophene) |
| 765 cm$^{-1}$: | 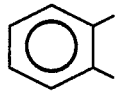 |
| 700 cm$^{-1}$: | 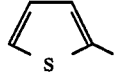 |

NMR Spectrum: as expected.

After the aqueous acidic solution has been made alkaline, the remaining 2-chlorobenzylamine is extracted with isopropyl ether. 2 extractions with equal volumes of ether and a distillation in a vacuum lead to the recovery of 29 g of 2-chlorobenzylamine.

EXAMPLE 3

50 g of 2-thiophene acetonitrile, 280 g of 2-chlorobenzylamine and 25 g of Raney nickel are introduced into a hydrogenation vessel of 350 ml capacity.

The mixture is hydrogenated at 50° C. at a pressure of 35±5 bars (3.5±0.5 MPa) until the theoretical amount of hydrogen has been absorbed.

The catalyst is filtered off and washed with methanol. The filtrate is concentrated and then distilled under a pressure of 0.3 mm Hg (40 Pa), as in example 1.

In this way, 65 g of N-(2-chlorobenzyl)-2-(2-thienyl)ethylamine are obtained.

Yield: 64.5% with respect to the 2-thiophene acetonitrile introduced.

I.R. Spectrum and elemental analysis are as expected.

EXAMPLE 4

20 g of Raney nickel, 280 g (1.95 mole) of 2-chlorobenzylamine and 500 ml of methanol are introduced into a hydrogenation reaction vessel of 3.5 l capacity. The temperature is brought to 50° C. and the hydrogen pressure to 25 bars (2.5 MPa).

100 g (0.80 mole) of 2-thiophene acetonitrile dissolved in 900 ml of methanol are then introduced by means of a meter pump. The addition takes 5 h.

When no more hydrogen is taken up, the catalyst is filtered off and washed with methanol. The methanol is evaporated under reduced pressure and the concentrate is treated as in example 1. In this way, 152 g of the expected product are obtained.

Yield: 75.5% with respect to the 2-thiophene acetonitrile introduced.

EXAMPLE 5

20 g (0.16 mole) of 2-thiophene acetonitrile, 45 g (0.32 mole) of 2-chlorobenzylamine, 5 g of 10% palladium-on-charcoal and 130 ml of methanol are introduced into a hydrogenation reaction vessel of 500 ml capacity.

The hydrogenation is conducted at 50° C. at a hydrogen pressure of 60±10 bars (6±1 MPa).

As soon as no more hydrogen is taken up, the catalyst ist filtered off and the solvent is evaporated in a vacuum.

The residue is taken up in 200 ml of isopropyl ether and the mixture is stirred for 1 h with 100 ml of 6N hydrochloric acid.

The product which crystallized is filtered off, washed with water, then with isopropyl ether and acetone, and is dried to constant weight at 50° C.

In this way, 22.9 g of the hydrochloride of N)(2-chlorobenzyl)-2-(2-thienyl)ethylamine are obtained.

Yield with respect to the 2-thiophene acetonitrile reacted: 80.0%. I.R. spectrum identical with that of the hydrochloride obtained in example 2.

On evaporation of the first ethereal phase, 7.8 g of 2-thiophene acetonitrile are obtained which can be recycled.

After alkanization the aqueous phase is extracted with isopropyl ether, from which 29.9 g of 2-chlorobenzylamine are isolated, which can be recycled.

EXAMPLE 6

20 g (0.16 mole) of 2-thiophene acetonitrile, 25 g (0.176 mole) of 2-chlorobenzylamine, 5 g of 10% palladium-on-charcoal and 150 ml of methanol are introduced into a hydrogenation reaction vessel of 500 ml capacity.

The hydrogenation is conducted at 50° C. at a hydrogen pressure of 60±10 bars (6±1 MPa).

The reaction mixture is then treated as in example No 4. In this way, 16.7 g of the hydrochloride of N-(2-chlorobenzyl)-2-(2-thienyl)ethylamine are obtained.

After evaporation of the first ethereal phase, 10.0 g of 2-thiophene acetonitrile are obtained which can be recycled.

The yield with respect to the 2-thiophene acetonitrile reacted: 82.5%

I claim:

1. A process for the preparation of N-(2-chlorobenzyl)-2-(2-thienyl)ethylamine, wherein 2-thiophene acetonitrile is reacted with 2-chlorobenzylamine and hydrogen in the presence of a hydrogenation catalyst.

2. A process according to claim 1, wherein the hydrogen pressure in the reaction vessel is from 1 to 10 MPa.

3. A process according to claim 2, wherein the hydrogen pressure is between 2.5 and 7 MPa.

4. A process according to claim 1, wherein the reaction is carried out at a temperature lower than 80° C.

5. A process according to claim 4, wherein the temperature is between 40° and 60° C.

6. A process according to claim 1, wherein the reaction is carried out in an alcohol as solvent.

7. A process according to claim 1, wherein the molar ratio of the 2-chlorobenzylamine to the 2-thiophene acetonitrile is between 1 and 5.

8. A process according to claim 7, wherein the catalyst is Raney nickel and the said molar ratio is between 2 and 4.

9. A process according to claim 7, wherein the catalyst is palladium and the said molar ratio is between 1 and 2.

* * * * *